(12) United States Patent
Gonon (10) Patent No.: US 10,758,678 B2
(45) Date of Patent: Sep. 1, 2020

(54) HYDRAULIC ASSEMBLY OF A GENERATOR OF MEDIUM-PRESSURE AND HIGH-PRESSURE PULSED OR NON-PULSED JETS

(71) Applicant: Boston Scientific Scimed, Inc., Maple Grove, MN (US)

(72) Inventor: Bertrand Gonon, Ternay (FR)

(73) Assignee: Boston Scientific Limited, Hamilton (BM)

( * ) Notice: Subject to any disclaimer, the term of this patent is extended or adjusted under 35 U.S.C. 154(b) by 904 days.

(21) Appl. No.: 15/107,267

(22) PCT Filed: Dec. 22, 2014

(86) PCT No.: PCT/FR2014/053514
§ 371 (c)(1),
(2) Date: Dec. 9, 2016

(87) PCT Pub. No.: WO2015/097398
PCT Pub. Date: Jul. 2, 2015

(65) Prior Publication Data
US 2017/0080156 A1 Mar. 23, 2017

(30) Foreign Application Priority Data
Dec. 23, 2013 (FR) ..................... 13 63494

(51) Int. Cl.
*A61M 5/30* (2006.01)
*A61B 17/3203* (2006.01)
(Continued)

(52) U.S. Cl.
CPC ....... *A61M 5/3007* (2013.01); *A61B 17/3203* (2013.01); *A61M 3/0233* (2013.01);
(Continued)

(58) Field of Classification Search
CPC .... A61M 5/3007; A61M 5/142; A61M 5/148; A61M 5/155; A61M 5/145; A61M 5/14;
(Continued)

(56) References Cited

U.S. PATENT DOCUMENTS 3,151,616 A * 10/1964 Selfon .................. A61M 5/148
128/DIG. 12
3,199,511 A * 8/1965 Kulick ................ A61M 5/1483
128/DIG. 12
(Continued)

FOREIGN PATENT DOCUMENTS

CA 2800152 A1 * 12/2011 .......... A61M 3/0275
CN 2701400 5/2005
(Continued)

OTHER PUBLICATIONS

International Search Report of International Application No. PCT/FR2014/053514, dated Apr. 22, 2015 (4 pages).
(Continued)

*Primary Examiner* — Nathan R Price
*Assistant Examiner* — Mark A Igel
(74) *Attorney, Agent, or Firm* — Bookoff McAndrews, PLLC (57) ABSTRACT

The present application relates to a hydraulic assembly of a generator of medium-pressure and high-pressure pulsed or non-pulsed jets. The hydraulic assembly includes a hydraulic pipe with a flexible deformable zone. The flexible deformable zone can have a state of rest and a shut-off state. The hydraulic assembly includes a unit configured to hold the hydraulic pipe with a first clamp and a second clamp holding the hydraulic pipe on each side of the flexible deformable zone. The unit can form an open space between the first clamp and the second clamp.

20 Claims, 4 Drawing Sheets

(51) Int. Cl.
*A61M 3/02* (2006.01)
*A61B 17/00* (2006.01)

(52) U.S. Cl.
CPC . *A61M 3/0275* (2013.01); *A61B 2017/00154* (2013.01); *A61B 2217/007* (2013.01); *A61M 2205/12* (2013.01)

(58) Field of Classification Search
CPC .... A61M 5/00; A61M 5/1483; A61M 5/1486; A61M 2005/14573; A61M 3/0233; A61M 3/0275; A61B 17/3203; A61B 2217/007; A61B 2217/00154
See application file for complete search history.

(56) References Cited

U.S. PATENT DOCUMENTS

| | | | | |
|---|---|---|---|---|
| 4,126,132 | A * | 11/1978 | Portner | A61M 5/14224 128/DIG. 12 |
| 4,397,639 | A * | 8/1983 | Eschweiler | A61M 5/142 128/DIG. 12 |
| 4,525,156 | A * | 6/1985 | Benusa | A61M 3/0233 604/28 |
| 4,537,561 | A * | 8/1985 | Xanthopoulos | A61M 5/142 128/DIG. 12 |
| 5,163,909 | A * | 11/1992 | Stewart | A61M 5/1486 128/DIG. 12 |
| 5,181,910 | A * | 1/1993 | Scanlon | A61M 5/172 128/DIG. 12 |
| 5,478,211 | A * | 12/1995 | Dominiak | A61M 5/142 417/234 |
| 5,482,438 | A * | 1/1996 | Anderson | A61M 5/142 417/44.1 |
| 5,482,446 | A * | 1/1996 | Williamson | A61M 5/142 417/234 |
| 5,681,294 | A * | 10/1997 | Osborne | A61M 5/142 604/131 |
| 5,776,104 | A * | 7/1998 | Guignard | A61M 3/0233 604/131 |
| 6,083,189 | A * | 7/2000 | Gonon | A61B 17/3203 604/118 |
| 9,095,656 | B2 * | 8/2015 | Gonon | A61B 17/3203 |
| 2005/0090778 | A1 * | 4/2005 | Gonon | A61B 17/32037 604/140 |
| 2012/0266965 | A1 | 10/2012 | Hariharesan et al. | |
| 2013/0144207 | A1 * | 6/2013 | Gonon | A61B 17/3203 604/70 |
| 2017/0080156 | A1 * | 3/2017 | Gonon | A61M 3/0233 |

FOREIGN PATENT DOCUMENTS

| | | | |
|---|---|---|---|
| CN | 1973781 | 6/2007 | |
| CN | 201299648 | 9/2009 | |
| CN | 102958459 | 3/2013 | |
| JP | 2001314408 | 11/2001 | |
| JP | 3133453 | 7/2007 | |
| JP | 3133453 U * | 7/2007 | ......... A61M 39/281 |
| JP | 2013502980 | 1/2013 | |
| JP | 2013526957 | 6/2013 | |
| WO | WO-9749441 A1 * | 12/1997 | ......... A61B 17/3203 |
| WO | WO 2011/148333 A1 | 12/2011 | |
| WO | WO-2011148333 A1 * | 12/2011 | ......... A61B 17/3203 |

OTHER PUBLICATIONS

Mathieu Pioche et al.: "High-pressure jet injection of viscous solutions for endoscopic submucosal dissection: a study on ex vivo pig stomachs", Surgical Endoscopy, vol. 28, No. 5, Jan. 3, 2014 (Jan. 3, 2014), pp. 1742-1747.

Mathieu Pioche et al.: "High pressure jet injection of viscous solutions for endoscopic submucosal dissection (ESD): first clinical experience," Endosc Int Open, 03: E368-E372, 2015.

* cited by examiner

HYDRAULIC ASSEMBLY OF A GENERATOR OF MEDIUM-PRESSURE AND HIGH-PRESSURE PULSED OR NON-PULSED JETS

This application is the U.S. national phase entry under 35 U.S.C. § 371 of International PCT Application No. PCT/FR2014/053514, filed on Dec. 22, 2014, which claims priority to French Application No. 1363494, filed on Dec. 23, 2013, the entirety of each of which is incorporated by reference herein.

The present application relates to a hydraulic assembly of a generator of medium-pressure and high-pressure pulsed or non-pulsed jets, specifically for a medium-pressure and high-pressure pulsed or non-pulsed jets generator of intended for medical or surgical interventions, for example using a dosed or undosed sterile or therapeutic liquid, or a dosed or undosed liquid medium, containing cells or microorganisms or for implementing a treatment or injection procedure.

More particularly, the present application concerns a hydraulic assembly configured to connect a disposable flexible pouch of medical liquid to a handpiece, for example a catheter, such as a catheter configured at least to deliver a liquid by jets, for example an injection catheter or a dual-function catheter.

Such a flexible pouch is generally pressurized within a chamber of a generator of pulsed or non-pulsed jets where the pressure is controlled by means of a compressed gas and in which the ejection of the liquid out from the flexible pouch is for example pulsed and sequenced by means of a hydraulic sequencer.

Such a generator is described, for example, e, in application WO2011148333.

To guarantee better hygiene and sterility of the hydraulic assembly within such a generator, starting at least from a flexible pouch on up to a catheter, it is particularly convenient to use an assembly, generally called a cartridge, constituting a single fully replaceable and interchangeable functional unit, otherwise called a single-use kit, for example.

Therefore, the present application aims to propose an easy-to-use disposable hydraulic assembly, for easy and fast installation in and/or removal from a generator of pulsed or non-pulsed jets.

For this purpose, a hydraulic assembly for a generator of medium- and high-pressure pulsed or non-pulsed jets is proposed, including:

a hydraulic line comprising a soft deformable zone allowing a state of rest and a closed state, and a case configured to hold the hydraulic line, characterized in that the case comprises a first clamp and a second clamp, the first clamp and the second clamp holding the hydraulic line on both sides of the soft deformable zone, and in that the case also has an open space, defined between the first clamp and the second clamp.

Here "open" is understood to mean that the space is specifically configured to permit an obturator to access the soft deformable zone to be able to close it.

The hydraulic line, outside of the soft deformable zone, is for example formed of a tube, for example reinforced, configured to minimize the deformations in order to limit any loss of pressure when the assembly is placed in a high- and medium-pressure chamber of a generator and is connected to a pouch of fluid to be injected.

The soft deformable zone is configured so that at least an obturator of a generator of pulsed jets can clamp it, in order to close a section if necessary. When it is used, a flow of liquid coming from the pouch is then interrupted when the soft deformable zone is in the closed state, and a pulse is then emitted when the soft deformable zone is in a state of rest. In other words, the generator obturator is open when the soft deformable zone is at rest, and is closed when it is in the closed state.

Such a case is thus particularly convenient and leaves the soft deformable zone visible and easy to access.

Therefore, it is particularly easy to handle the assembly to position it in the generator, by connecting it firstly to a pouch of fluid and secondly to a handpiece, for example, while being able to better monitor a positioning of the soft deformable zone compared to an obturator to form the pulses.

According to one interesting example of embodiment, the hydraulic line comprises:

a fluid-intake line, a fluid-output line, and a connection line, between the fluid-intake line and the fluid-output line, configured to connect the fluid-intake line to the fluid-output line and comprising the soft deformable zone.

According to one preferred embodiment, the case holds the hydraulic line by the connection line, and the first clamp holds a part of the connection line upstream of the soft deformable zone, and the second clamp holds a part of the connection line downstream from the soft deformable zone.

In this application, the terms "upstream" and "downstream" refer to a direction of flow of fluid in the hydraulic assembly when it is connected to a pouch of fluid in a generator.

According to a more particular example, the first clamp surrounds a first end of the connection line and the second clamp surrounds a second end of the connection line so that the soft deformable zone is located, or even delimited, in the space between the first clamp and the second clamp.

According to a particularly convenient example, the fluid-intake line is connected to the connection line by a first tip. For example, the first tip is bent.

According to another particularly convenient example, the fluid-output line is connected to the connection line by a second tip. And for example, the second tip is straight.

According to a preferred embodiment, the soft deformable zone is formed by a silicone tube.

The silicone tube advantageously has a hardness ranging from approximately 50 to approximately 70 ShA (shore A), or even preferably 60 ShA.

According to another interesting embodiment, the case also comprises an anchoring leg configured to affix the case in a high-pressure chamber of generator of pulsed or non-pulsed jets.

According to yet another interesting embodiment, the case also comprises a hook configured to hold a pouch.

Advantageously, the case is positioned higher than the pouch within the chamber of the generator, which makes it possible, for example, to hold the pouch straight. Such a configuration also makes it possible to limit the bubbles that would be formed in the hydraulic line.

The assembly also comprises, for example, a first mouth configured to connect the assembly to a pouch filled with fluid. Advantageously, the first mouth comprises a first branch configured to be connected to one end of the hydraulic line and a second branch configured to be connected [to] the pouch filled with fluid. Moreover, the first branch and the second branch optionally form a bend. That makes it easier to hang the pouch.

The assembly optionally also comprises a conical tip. The conical tip comprises, for example, a broad end and a narrow end. And preferably, the hydraulic line is connected to the broad end of the conical tip.

According to one embodiment, the assembly also comprises a connection line with a handpiece. For example, the connection line is then connected to the conical tip by its narrow end if the assembly comprises a conical tip.

According to one example of embodiment, the invention will be readily understood and its advantages will better appear upon reading the following detailed description, which is given as an indication and is by no means restrictive, in reference to the attached drawings, in which:

FIG. 3 shows, in detail, part of a hydraulic line according to one example of embodiment of this invention to make a connection with a flexible pouch, FIG. 4 shows, in detail, a part of a hydraulic line according to one example of embodiment of this invention with a soft deformable zone.

The identical components shown in FIGS. 1 to 6 are identified by identical numerical references.

Figure 1:
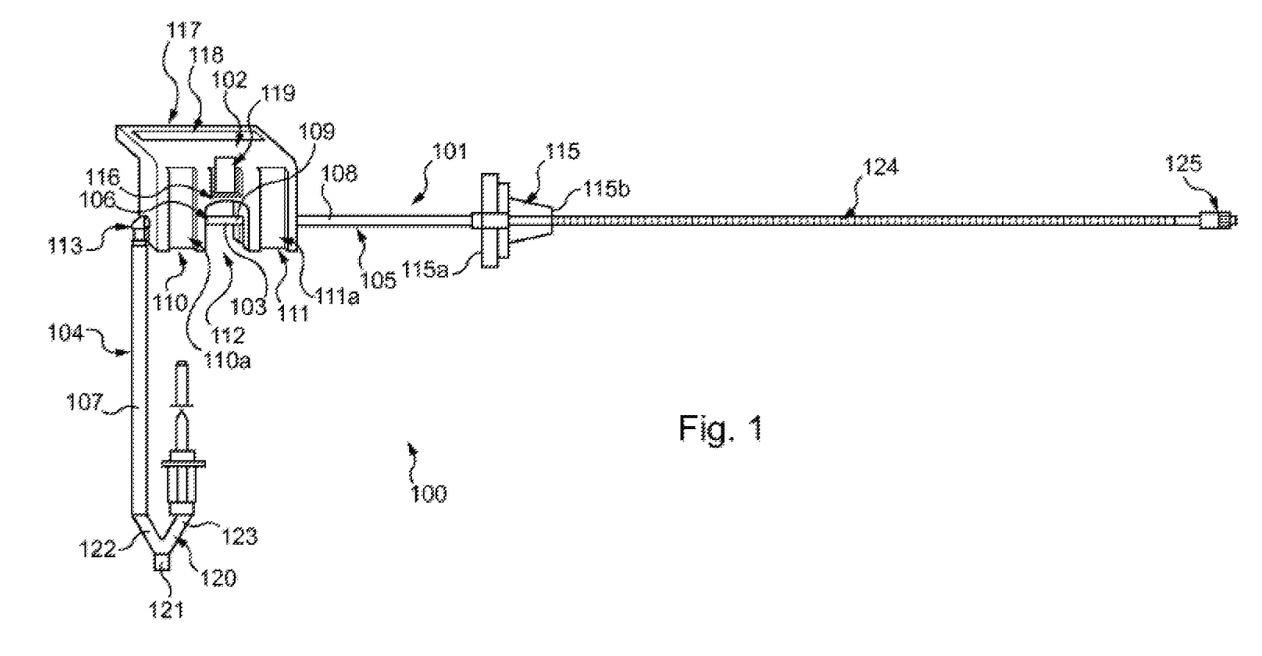
FIG. 1 shows a hydraulic assembly according to one example of embodiment of this invention viewed face on, FIG. 2 shows a hydraulic assembly according to one example of embodiment of this invention viewed from the back.

FIG. 1 shows a hydraulic assembly 100 according to one example of embodiment of this invention.

The hydraulic assembly 100 comprises mainly a hydraulic line 101 and a case 102.

The hydraulic line 101 comprises a soft deformable zone 103. The soft deformable zone 103 is configured to assume a state of rest and a closed state, i.e. a deformed state in which it is clamped, for example by an obturator, so that the line is closed.

In general, outside the soft deformable zone 103, the hydraulic line 101 is configured to maintain a pressure of the fluid, i.e. to limit load losses. For that purpose, it is, for example, the least deformable possible.

Figures 2, 3, 4:
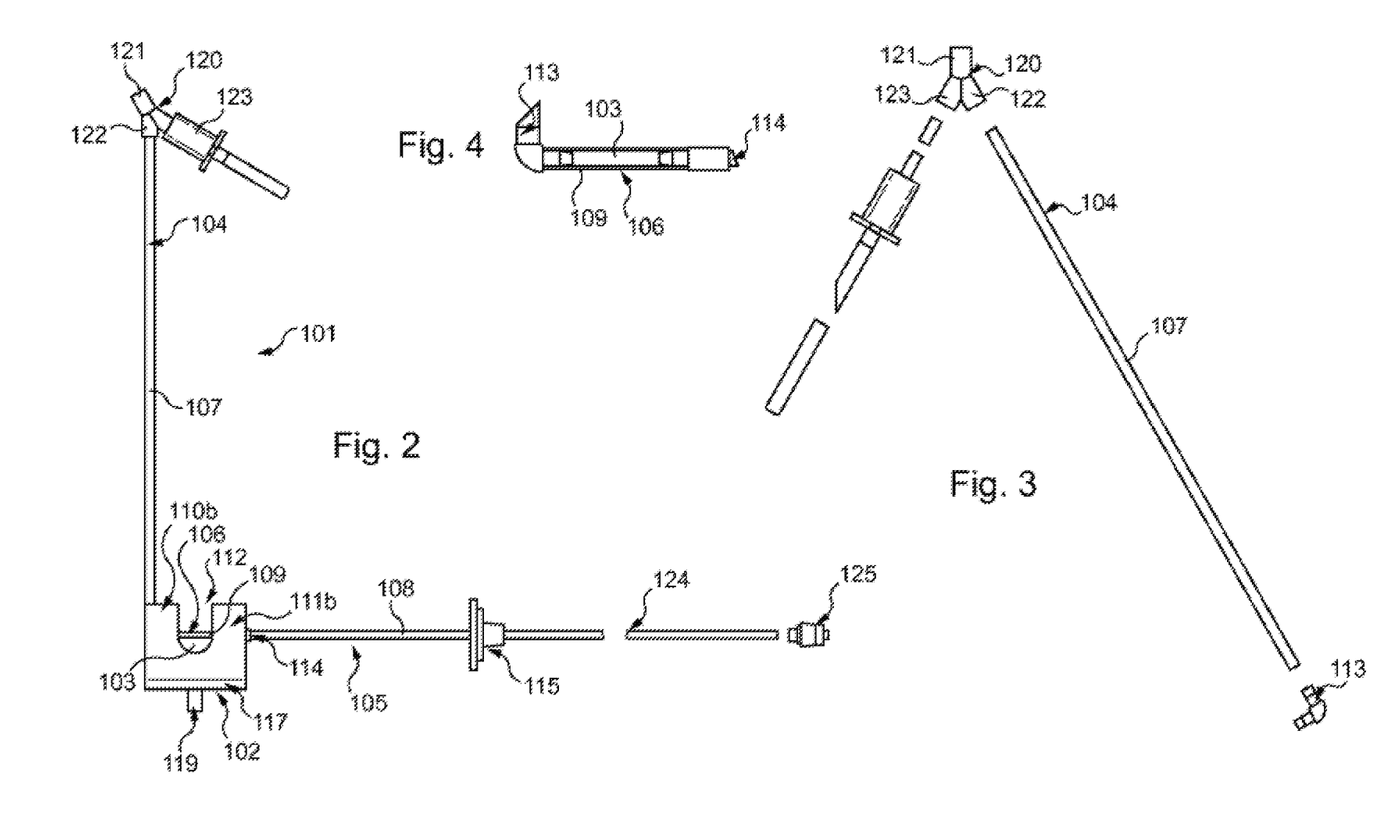

The difference between the closed state and the state of rest corresponds to a variation of section of the soft deformable zone 103, so that it is possible, when it returns to the state of rest, to generate a pulse of fluid, thanks specifically to a generator of pulsed jets as shown, for example, in FIG. 3.

The soft deformable zone 103, for example, is made by a part of the hydraulic line 101 having a wall with reduced thickness compared to the rest of the hydraulic line 101, or, for example, by a section of the hydraulic line 101 made of a softer material, i.e. more easily deformable than the rest of the hydraulic line 101. The soft deformable zone 103, for example, is made of a single holder with the hydraulic line 101 or by an added component, for example with a thinner wall and/or made of a softer material.

The hydraulic line 101 comprises three parts here. A first part 104 allows an intake of fluid into the soft deformable zone 103 when the hydraulic assembly 100 is connected with a flexible pouch 202 (shown in FIG. 6). A second part 105 allows an output of fluid from the soft deformable zone 103, for the purpose, for example, of a connection with a handpiece 300 (shown in FIG. 6). A third part 106 makes it possible to connect the first part 104 to the second part 105 and comprises here the soft deformable zone 103.

In this example of embodiment, the hydraulic line 101 comprises three lines 107, 108, and 109, each forming one of the parts of the hydraulic line 101. Thus, the first part 104 comprises, for example, a fluid-intake line 107, the second part 105 comprises a fluid-output line 108, and the third part 106 comprises a connection line 109.

Here, the fluid-intake line 107 has a length of a few tens of centimeters, and an internal diameter of a few millimeters. It is, for example, composed of a reinforced tube, or even made of a non-deformable material. The fluid-intake line 107 is connected to the connection line 109 by a first tip 113. In other words, the first tip 113 is configured to transfer fluid from the fluid-intake line 107 to the connection line 109. Moreover, the first tip 113 here is bent. It has, for example, a right-angle fold. Therefore, once the hydraulic assembly 100 is mounted in a pressure generator as shown, for example, in FIG. 6, the fluid-intake line 107 is roughly vertical while the connection line 109 is roughly horizontal. In one embodiment in which the hydraulic line 101 would be made of a single line, the orientation reference between the first part 104 and the third part 106, for example, is made by a bent framework, which would come to surround the hydraulic line 101 where the bend would be meant to be positioned.

As also shown in FIGS. 3 and 4, the first tip 113 is, for example, first inserted into a first end of the fluid-intake line 107 and then into a first end of the connection line 109. The fluid-intake line 107 firstly, and the connection line 109 secondly are then configured to form a tight connection with the first tip 113.

According to one particular example of embodiment, the connection line 109 is a silicone tube with a hardness ranging from approximately 50 to 70 ShA, for example 60 ShA (shore A). It has, for example, an internal diameter of a few millimeters, and a length of a few centimeters.

Therefore, as shown more precisely in FIG. 4, the soft deformable zone 103 is formed by the assembly of the connection line 109.

Figure 5A:
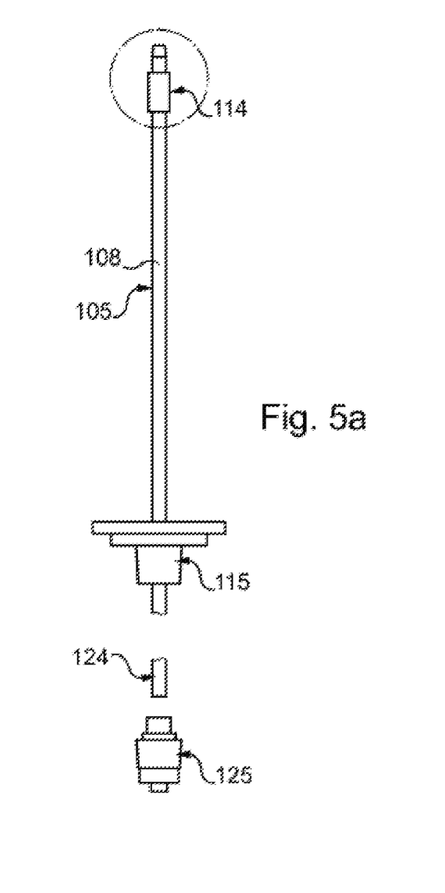
FIG. 5 shows, in detail, a part of a hydraulic line according to one example of embodiment of this invention to make a connection with a handpiece.
Figure 5B:
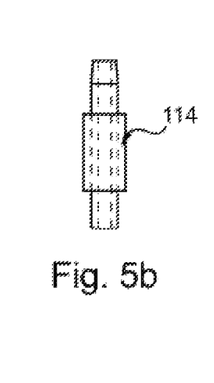
Figure 5C:
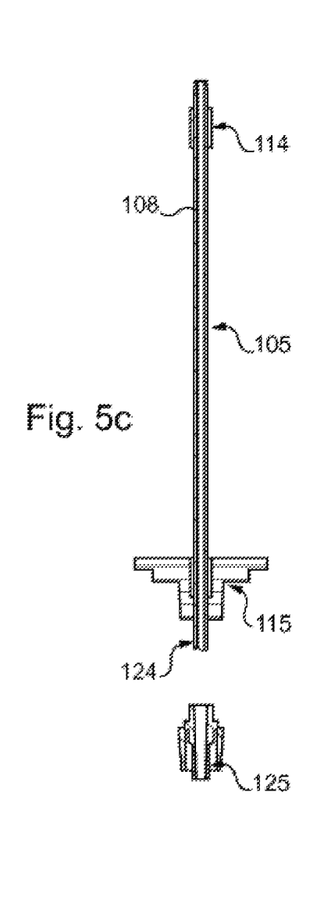

The fluid-output line 108 is shown in greater detail in FIGS. 5a and 5c. It has, for example, a length of a few tens of centimeters, an internal diameter of a few millimeters. It is, for example, also made of a reinforced tube, or even a non-deformable material, like the fluid-intake line 107.

The fluid-output line 108 is connected to the connection line 109 by a second tip 114, shown, for example, in FIG. 5b.

Figure 6:
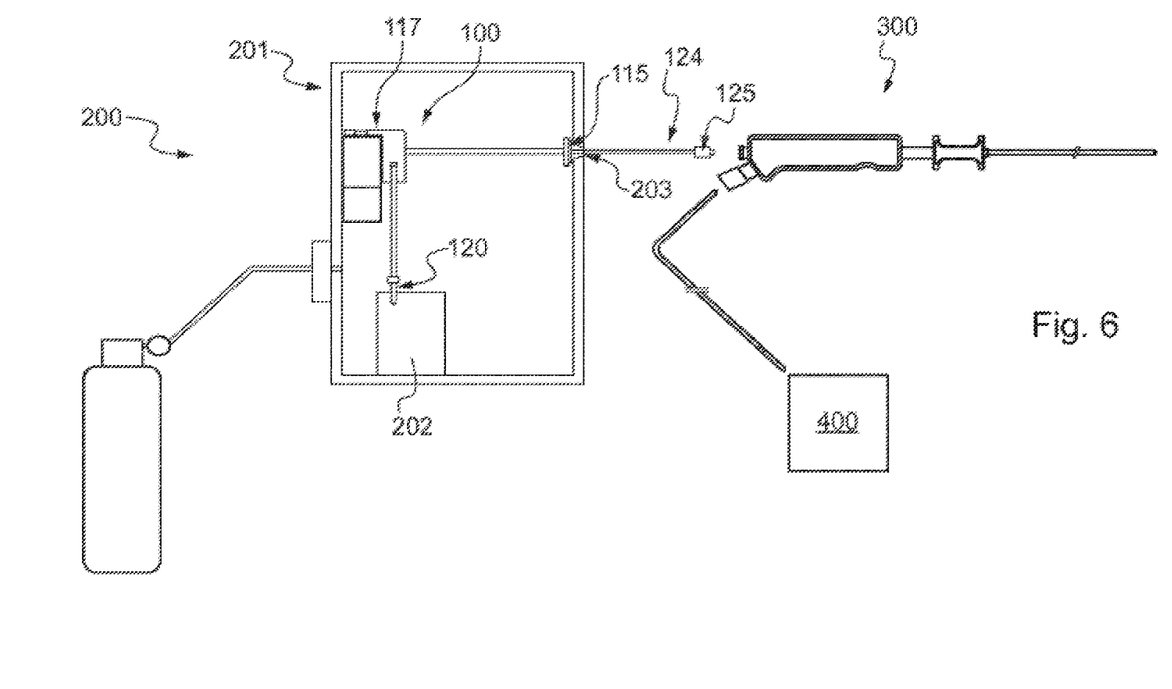
FIG. 6 shows a generator of medium- and high-pressure pulsed jets to which a dual-function catheter is connected and comprising a hydraulic assembly according to one example of embodiment of this invention.

The second tip 114 is preferably straight, as shown in FIGS. 1, 2, 4 and 5, or bent in a configuration as shown in FIG. 6. If it is bent, the second tip 114 has, for example, a right angle. For example, the connection line 109 and the fluid-output line 108 are advantageously roughly in the same horizontal plane once the hydraulic assembly 100 is mounted in a generator 200. The second tip 114, for example, is configured to orient the connection line 109 and the fluid-output line 108 roughly in the same horizontal plane, in one embodiment in which the hydraulic line 101 would be made of a single line, the orientation reference between the third part 106 and the second part 105, if applicable, is made, for example, by a bent framework which would come to surround the hydraulic line 101 where the bend would be meant to be positioned.

Just as above, to make the junction between the connection line 109 and the fluid-output line 108, the second tip 114 is, for example, inserted first into a second end of the connection line 109 and then into a first end of the fluid-output line 108, as shown in FIGS. 4 and 5. The fluid-output line 108 firstly, and the connection line 109 secondly, are then configured to form a sealed connection with the second tip 114.

FIG. 1 also shows that, in order to hold the hydraulic line 101 to position it in a generator, the case 102 has a holding system which is here specifically composed of a first clamp 110 and a second clamp 111. The case 102 also has a space 112, which is defined here between the first clamp 110 and the second clamp 111. The space 112 is configured, in the case 102, to receive the soft deformable zone 103, in a closed or not closed state, as well as an obturator (not shown) configured so as to close a section of the soft deformable zone, for example occasionally or at regular or irregular intervals of time.

The first clamp 110 and the second clamp 111 are each made of two jaws (respectively numbered 110a and 110b for the first clamp 110, and 111a and 111b for the second clamp 111) which are rigid here and also interconnected by a rigid connection. By convention, the jaws 110a and 111a are defined here as being the jaws of a front face of the case 102, and the jaws 110b and 111b are defined here as being the jaws of a back face of the case 102.

Therefore the jaws 110a and 110b of the first clamp 110 define between them a guide, which for example here is U-shaped, into which the hydraulic line 101 comes to be inserted, and in the same fashion, the jaws 111a and 111b of the second clamp 111 therefore define between them a guide, which for example here is also U-shaped, into which the hydraulic line 101 comes to be inserted. For that, the first clamp 110 and the second clamp 111 each comprise, for example, at least one pawl (not shown), or even two pawls facing each other, configured to insert the hydraulic line 101 easily into each clamp and to prevent an easy removal of the hydraulic line 101.

If the hydraulic line 101 has a bend between the first part 104 and the third part 106, and/or a bend between the third part 106 and the second part 105, those are formed upstream of the case 102 for the bend between the first part 104 and the third part 106, and downstream of the case 102 for the bend between the third part 106 and the second part 105. In other words, the case 102 is then localized between the two bends. Therefore, the third part 106, which has the soft deformable zone 103, is held as straight as possible by the first clamp 110 and the second clamp 111 of the case 102. In other words, the first clamp 110 and the second clamp 111 are aligned; an internal wall of the jaw 110a and an internal wall of the jaw 111a are coplanar, and an internal wall of the jaw 110b and an internal wall of the jaw 111b are coplanar.

The term "internal" wall here indicates a wall of a jaw defining the guide in the bottom of which the hydraulic line 101 is blocked. At least one of the internal walls of the jaws 110a and 110b of the first clamp 110 and the internal walls of the jaws 111a and 111b of the second clamp 111 has a pawl to block the hydraulic line 101.

Moreover, in the embodiment in which the fluid-intake line 107 is connected to the connection line 109 by the first tip 113, the first clamp 110 surrounds at least part of the first tip 113 inserted into the connection line 109, specifically so as to reinforce the tight seal between the connection line 109 and the first tip 113. In the same fashion, in the embodiment in which the fluid-output line 108 is connected to the connection line 109 by the second tip 114, the second clamp 111 surrounds at least part of the second tip 114 inserted into the connection line 109, specifically so as to reinforce the tight seal between the connection line 109 and the second tip 114.

In this example of embodiment, the space 112 is defined by the distance separating the first clamp 110 and the second clamp 111 according to their direction of alignment. In other words, here it has a height limited only on one side by a bridge 116 joining the first clamp 110 and the second clamp 111, a limitless depth, and a width limited firstly by the first clamp 110 and secondly by the second clamp 111.

Therefore the case 102 is particularly simple to manufacture, specifically by molding. And a space 112 thus defined makes it possible to observe the soft deformable zone 103 more easily. Moreover, the same case 102 is thus adaptable to different hydraulic lines 101 whose sizing, of the soft deformable zone 103 specifically, can be variable as needed.

Here, for example, the case 102 has small overall dimensions, for example of a few centimeters on the side.

Advantageously, the case 102 has an anchoring leg 117. The anchoring leg 117 is specifically configured to affix the case 102 in a high-pressure chamber 201 of a generator of pulsed jets 200 (or in a generator of non-pulsed jets), as shown in FIG. 6.

Here, the anchoring leg 117 connects the first clamp 110 and second clamp 111. In the embodiment presented here, the anchoring leg extends roughly in orthogonal fashion to the clamps 110 and 111.

Moreover, the anchoring leg 117 here is primarily made of a loop, in other words it has a hole 118 enabling the anchoring leg 117 to form a handle. Thanks to the hole 118, the anchoring leg 117 is also configured here, for example, to surround a block, for example located in the high pressure chamber 201 of the generator 200. Therefore, the hydraulic assembly 100 can be easily handled while being carried by the case 102 and can be easily positioned in a chamber 201 of a generator 200 by the case 102.

In the example of embodiment shown in FIGS. 1 and 2, the case 102 also optionally has a hook 119 configured to hang the pouch 202 there. The case 102 for example is positioned in the chamber higher than the pouch 202, such that the case 102 is therefore configured to hold the pouch 202 straight.

In reference to FIGS. 1 to 3, the hydraulic assembly 100 also has here a first mouth 120.

The first mouth 120 is configured to connect the hydraulic assembly 100 to the pouch 202 filled with fluid.

The first mouth 120 here has two branches 122 and 123. A first branch 122 is configured to be connected to one end of the hydraulic line 101, and a second branch 123 is configured to be connected to the pouch 202 filled with fluid, with the second branch 123 and the first branch 122 forming a bend 121 between them. Such a bend 121 specifically makes it easy to affix the pouch 202 in the chamber 201, for example so as to hold the pouch straight, specifically when it is affixed on the hook 119.

According to one alternative embodiment, the first mouth 120 has a third branch, for example, which then forms the bend 121 and which is configured to form a subsidiary access to the contents of the pouch 202, or even to another pouch.

In this example of embodiment, the first branch 122 of the first mouth 120 is inserted into a first end of the hydraulic line 101, which corresponds at a second end of the fluid-intake line 107, as shown, for example, in FIGS. 2 and 3.

In reference to FIGS. 1, 2 and 5, the hydraulic assembly 100 here also has a conical tip 115. The conical tip 115 has a broad end 115a and a narrow end 115b (represented in FIG. 1). The hydraulic line 101 is connected to the broad end 115a of the conical tip 115 by a second end, which here, for example, is the second end of the fluid-output line 108. Here, the second end of the hydraulic line 101 is inserted, for example, into the broad end 115a of the conical tip 115. The connection can moreover be reinforced with adhesive if necessary.

Therefore, once the hydraulic assembly 100 is mounted in the generator 200, the conical tip 115 is positioned in the chamber 201 with its narrow end 115b in an outlet hole 203 of the generator 200. In this manner, the greater the pressure in the chamber 201, the further the conical tip 115 is inserted into the outlet hole 203, so as to guarantee the seal of the chamber 201. For this purpose, the conical tip is made, for example, out of a soft polymer or an elastomer, for example out of rubber.

Optionally, the hydraulic assembly 100 also has a connection line 124 to connect it with a handpiece 300.

The connection line 124 has a length, for example, of a few tens of centimeters, and an internal diameter of a few millimeters. It is specifically configured to maintain the water pressure constant without deforming the tubing, i.e. the line 124. It can moreover have a certain flexibility to make it easier to handle the handpiece 300.

The connection line 124 has a first end that is connected to the narrow end 115b of the conical tip 115, and it has a second end that has a connector 125 to effectuate a fluid connection with the handpiece 300 in order to deliver pulsed or non-pulsed jets. According to one example of embodiment, the connection line 124 and the fluid-output line 108, or even the hydraulic line 101, form one single line which traverses the conical tip 115.

FIG. 6 thus shows a generator of pulsed jets 200 that has a hydraulic assembly 100 as described above.

More precisely, the generator of pulsed jets 200 has a high-pressure chamber 201.

The high-pressure chamber 201 is pressurized, for example, by a pressurized gas generator.

A flexible pouch 202, filled with fluid, is situated here in the chamber 201.

The hydraulic assembly 100 is connected to the pouch 202 by the first mouth 120.

It is also hung in the chamber 201 by the anchoring leg 117, so that the case is roughly positioned above the pouch 202 and the first part 104 of the hydraulic line 101 is roughly vertical.

Thus, according to place available in the chamber 201 to hang the case 102, it is more convenient to have a bend between the second part 105 and the third part 106 of the hydraulic line 101. In other words, the configuration of the chamber 201 helps to determine whether it is preferable for a second tip 114 connecting a fluid-output line 108 to a connection line 109, when the hydraulic line 101 is made of several lines, to be straight or bent.

In addition, the conical tip 115 of the hydraulic assembly 100 is positioned in an outlet hole 203 of the generator 200 with its broad end 115a oriented towards the inside of the chamber 201 and its narrow end 115b oriented towards the outside of the chamber 201. So, the greater the pressure in the chamber 201, the further the tip 115 is inserted into the hole 203 to guarantee the seal of the chamber 201.

Lastly, the hydraulic assembly is extended outside the chamber 201 by the connection line 124 in order to make it possible to connect the generator 200 to a handpiece 300. In other words, the hydraulic assembly 100 is intended to be placed partly inside a chamber 201 of the generator 200 and partly outside the chamber 201 of the generator 200.

More particularly, the handpiece is then connected to the connector 125. In other words, the connector 125 allows a sealed connection between the hydraulic assembly 100 and a handpiece 300.

A hydraulic assembly 100 according to the invention thus constitutes a single-use kit, for example, to connect a pouch 200 to a handpiece 300 in sealed fashion, making it possible to generate pulses once placed in a chamber 201 of a pulsed jet generator 200.

The handpiece 300 is then connected, for example, firstly to the pulsed jet generator 200 for a fluid supply, and secondly to an electric generator 400, for example, for an electric power supply. Such a handpiece 300 is, for example, a dual-function catheter.

Of course, this invention is not limited to the preceding description, but extends to any variant within the framework of the following claims.

The invention claimed is:

1. A hydraulic assembly of a generator of fluid jets, comprising:
   a hydraulic line that has a deformable zone having a resting open state and a closed state; and
   a case configured to hold the hydraulic line;
   wherein the case comprises a first clamp and a second clamp, wherein the first clamp and the second clamp hold the hydraulic line on both sides of the deformable zone, and wherein the first clamp and the second clamp define an open space therebetween, and wherein the open space is a U-shaped opening in the case configured to provide access to the deformable zone from outside the case,
   wherein the case further comprises an anchoring leg connecting the first clamp and the second clamp, and wherein the anchoring leg extends transverse to the first clamp and the second clamp, and
   wherein the anchoring leg includes a hole such that the anchoring leg forms a handle.

2. The assembly according to claim 1, wherein the hydraulic line comprises:
   a fluid-intake line;
   a fluid-output line; and
   a connection line, between the fluid-intake line and the fluid-output line, configured to connect the fluid-intake line to the fluid-output line and comprising the deformable zone.

3. The assembly according to claim 2, wherein the case holds the hydraulic line by the connection line, wherein the first clamp holds part of the connection line upstream of the deformable zone, and wherein the second clamp holds part of the connection line downstream from the deformable zone.

4. The assembly according to claim 2, wherein the fluid-intake line is connected to the connection line by a first tip, and wherein the first tip is bent.

5. The assembly according to claim 4, wherein the fluid-output line is connected to the connection line by a second tip, and wherein the second tip is straight.

6. The assembly according to claim 1, wherein the deformable zone includes a silicone tube, and wherein the silicone tube has a hardness ranging from approximately 50 ShA to approximately 70 ShA.

7. The assembly according to claim 1, wherein the anchoring leg is configured to affix the case in a high-pressure chamber of the generator in order to pressurize fluid delivered by the assembly via a compressed gas within the high-pressure chamber, and wherein the anchoring leg is configured to surround a block located in the high-pressure chamber to affix the case in the high-pressure chamber.

8. The assembly according to claim 1, wherein the case has a hook configured to hold a pouch, wherein the hook is positioned on the case between the first clamp and the second clamp.

9. The assembly according to claim 1, further including a first mouth configured to connect the assembly to a pouch filled with fluid, wherein the first mouth has a first branch configured to be connected to one end of the hydraulic line and a second branch configured to be connected to the pouch filled with fluid, with the second branch and the first branch forming a bend.

10. The assembly according to claim 1, further including a conical tip, with a broad end and a narrow end, the hydraulic line being connected at the broad end of the conical tip.

11. A hydraulic assembly of a generator of a fluid jet, comprising:
a hydraulic line that includes a deformable zone having a resting open state and a closed state, wherein the hydraulic line includes:
a fluid-intake line;
a fluid-output line;
a connection line, between the fluid-intake line and the fluid-output line, configured to connect the fluid-intake line to the fluid-output line and comprising the deformable zone; and
a mouth configured to connect the hydraulic assembly to a pouch filled with fluid, and
wherein the fluid-intake line is connected to the connection line by a first tip, wherein the first tip is bent, and wherein the fluid-output line is connected to the connection line by a second tip, and wherein the second tip is straight, and
wherein the mouth includes a first branch, a second branch, and a bend between the first branch and the second branch, wherein the first branch is configured to be connected to one end of the hydraulic line, and wherein the second branch is configured to be connected to the pouch; and
a case configured to hold the hydraulic line;
wherein the case comprises a first holding portion and a second holding portion, the first holding portion and the second holding portion holding the hydraulic line on both sides of the deformable zone, and wherein the case has a U-shaped open space between the first holding portion and the second holding portion to provide access for a medical device to at least a portion of the deformable zone from outside the case, and
wherein the case further comprises an anchoring leg and a hook, wherein the anchoring leg extends orthogonally from the first holding portion and the second holding portion, wherein the anchoring leg includes a hole such that the anchoring leg forms a handle and such that the anchoring leg is configured to surround a block located in the high-pressure chamber to affix the case in a high-pressure chamber of the generator in order to pressurize fluid delivered by the assembly via a compressed gas within the high-pressure chamber, and wherein the hook is configured to hold a pouch and is positioned on the case between the first holding portion and the second holding portion.

12. The assembly according to claim 11, wherein the case holds the hydraulic line by the connection line, wherein the first holding portion holds part of the connection line upstream of the deformable zone, and wherein the second holding portion holds part of the connection line downstream from the deformable zone.

13. The assembly according to claim 11, wherein the deformable zone includes a silicone tube, and wherein the silicone tube has a hardness ranging from approximately 50 ShA to approximately 70 ShA.

14. A hydraulic assembly of a generator of a fluid jet, comprising:
a hydraulic line that has a deformable zone having a resting open state and a closed state, wherein the deformable zone includes a portion of the hydraulic line having at least one of a reduced wall thickness and a softer material as compared to adjacent portions of the hydraulic line, and wherein the hydraulic line includes:
a fluid-intake line;
a fluid-output line; and
a connection line, between the fluid-intake line and the fluid-output line, configured to connect the fluid-intake line to the fluid-output line and comprising the deformable zone;
a case configured to hold the hydraulic line, wherein the case includes a U-shaped open space between a first clamp and a second clamp to provide access for an obturator from outside the case, wherein at least a portion of the deformable zone of the hydraulic line is positioned within the U-shaped open space, and wherein the case includes an anchoring leg that couples the first clamp and the second clamp and extends orthogonally to the first clamp and the second clamp, and wherein the anchoring leg includes a hole such that the anchoring leg forms a handle;
a fluid pouch coupled to the fluid-intake line; and
a chamber configured to receive pressurized gas from a pressurized gas generator to pressurize fluid in the fluid pouch.

15. The assembly according to claim 14, further comprising a conical tip that has a broad end and a narrow end, wherein the hydraulic line is coupled to the broad end of the conical tip.

16. The assembly according to claim 15, wherein the case receives a part of the connection line upstream of the deformable zone, and a part of the connection line downstream from the deformable zone.

17. The assembly according to claim 14, wherein the deformable zone includes a silicone tube, and wherein the silicone tube has a hardness ranging from approximately 50 ShA to approximately 70 ShA.

18. The assembly according to claim 14, further including a first mouth configured to connect the assembly to a pouch filled with fluid, wherein the first mouth has a first branch configured to be connected to one end of the hydraulic line, a second branch configured to be connected to the pouch filled with fluid, and a third branch, wherein the third branch is between the first branch and the second branch and forms a bend.

19. The assembly according to claim 14, wherein the case is U-shaped, and the U-shaped open space lies between legs of the U-shaped case.

20. The assembly of claim 14, wherein the anchoring leg is configured to surround a block located in the chamber to affix the case in the chamber of the generator, and
wherein the case includes a hook configured to hold the fluid pouch, wherein the hook is positioned on the case between the first clamp and the second clamp.

* * * * *